(12) United States Patent
Schellenberger et al.

(10) Patent No.: US 7,122,334 B2
(45) Date of Patent: Oct. 17, 2006

(54) METHOD OF ASSAYING WASH PERFORMANCE OF ENZYMES ON A MICROTITER PLATE

(75) Inventors: Volker Schellenberger, Palo Alto, CA (US); Donald P. Naki, San Francisco, CA (US); Katherine D. Collier, Redwood City, CA (US); James T. Kellis, Jr., Portola Valley, CA (US); Joanne Nadherny, San Francisco, CA (US)

(73) Assignee: Genencor International, Inc., Palo Alto, CA (US)

( * ) Notice: Subject to any disclaimer, the term of this patent is extended or adjusted under 35 U.S.C. 154(b) by 35 days.

(21) Appl. No.: 10/899,751

(22) Filed: Jul. 26, 2004

(65) Prior Publication Data

US 2004/0261193 A1    Dec. 30, 2004

(51) Int. Cl.
*C12Q 1/34*    (2006.01)
(52) U.S. Cl. ........................................... 435/18; 435/23
(58) Field of Classification Search .................. 435/18, 435/19, 22, 23
See application file for complete search history.

(56) References Cited

U.S. PATENT DOCUMENTS

| | | | |
|---|---|---|---|
| 4,760,025 A | 7/1988 | Estell et al. ................. | 435/222 |
| 5,612,306 A | 3/1997 | O'Brien et al. .............. | 510/321 |
| 6,586,221 B1 | 7/2003 | Graycar et al. ............. | 435/219 |
| 2005/0089966 A1* | 4/2005 | David et al. ............... | 435/69.1 |

FOREIGN PATENT DOCUMENTS

| | | |
|---|---|---|
| EP | 0 352 244 | 6/1989 |
| EP | 0 130 765 | 2/1991 |
| EP | 0 739 982 | 10/1996 |
| WO | WO 91/06637 | 5/1991 |
| WO | WO 93/05134 | 3/1993 |
| WO | WO 95/10615 | 4/1995 |
| WO | WO 97/07202 * | 2/1997 |
| WO | WO 97/23593 | 7/1997 |
| WO | WO 97/41212 | 11/1997 |
| WO | WO 99/11769 | 3/1999 |
| WO | WO 99/11770 | 3/1999 |

OTHER PUBLICATIONS

Cayot et al. (1997) Anal. Biochem. 249:184-200.
Morris and Prato, (1982) Textile Research Journal 52(4):280-286.

* cited by examiner

*Primary Examiner*—Ralph Gitomer
(74) *Attorney, Agent, or Firm*—Genencor Inertnational, Inc.

(57) ABSTRACT

A microtiter method for assaying the wash performance of new enzymes and/or new detergent formulations is described.

11 Claims, 1 Drawing Sheet

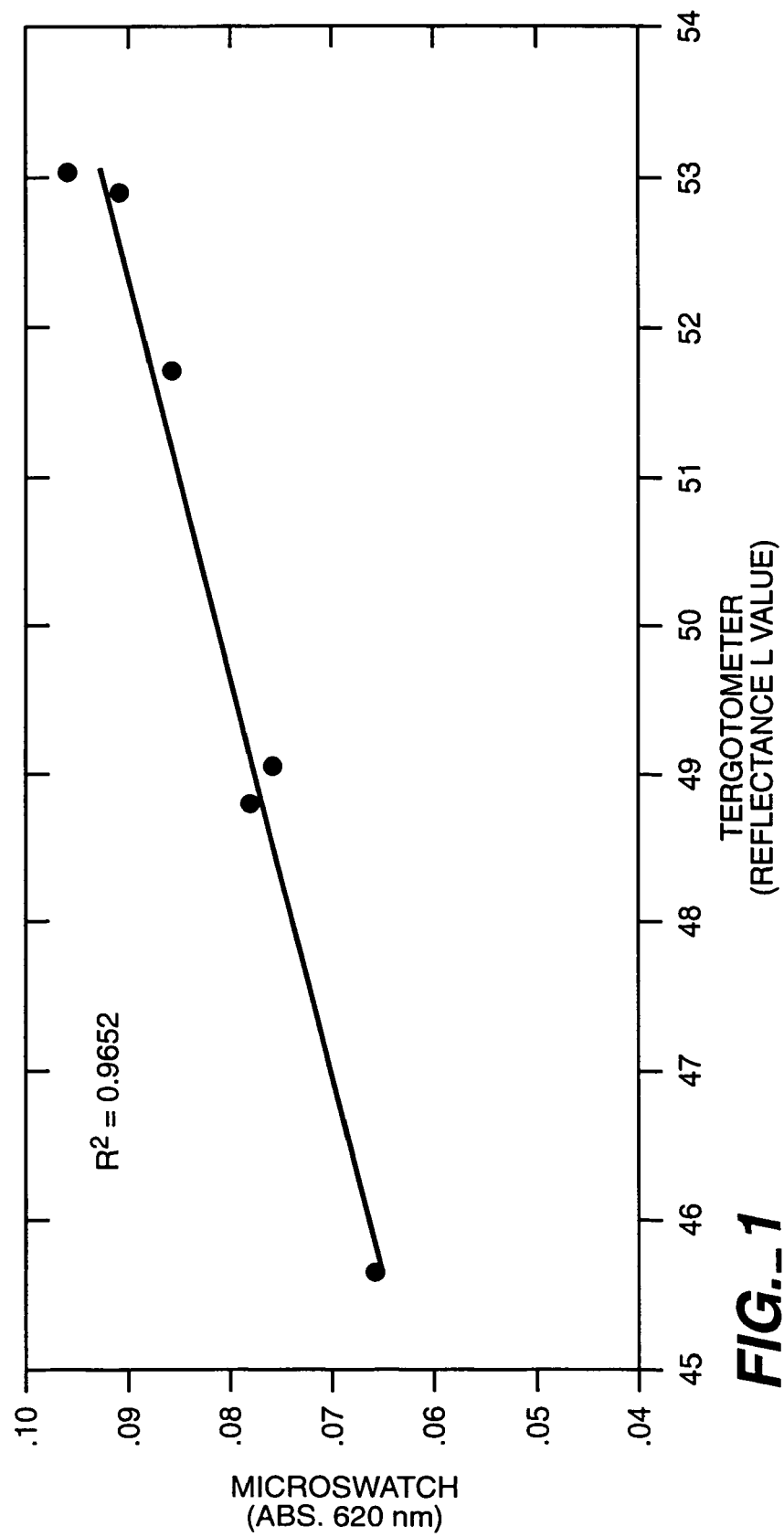
FIG._1

METHOD OF ASSAYING WASH PERFORMANCE OF ENZYMES ON A MICROTITER PLATE

The application claims priority from U.S. patent application Ser. No. 09/554,992, filed May 23, 2000 now abandoned; PCT/US98/27629, filed Dec. 23, 1998; and U.S. Provisional Application Ser. No. 60/068,796, filed December 24, 1997.

BACKGROUND OF THE INVENTION

Enzymes are a necessary part of many of the detergent compositions that are currently on the market and the inclusion of enzymes in detergent compositions will undoubtedly increase in the future. One of the most important challenges facing a detergent manufacturer today is the identification of new and improved enzymes and detergent compositions. New enzymes can and commonly do include variants of known enzymes.

Several factors can affect the determination of the "improvement" of a new enzyme over an precursor enzyme, i.e., the enzyme itself, the wash conditions, and the detergent composition that the enzyme is to be mixed with. For example, an enzyme that performs well in one detergent composition may not perform as well in another. Similarly, an enzyme and/or detergent composition may perform well under one set of wash conditions, i.e., Japanese, but not another, i.e., North American. However, identifying a new and improved enzyme or detergent composition can be a time consuming task. For example, in the wake of improved technology that can allow a researcher to produce large numbers of variants in a very short time, it has become critical for the researcher to be able to assay those variants rapidly, efficiently and effectively.

SUMMARY OF THE INVENTION

The present invention provides a method of assaying for a preferred enzyme including providing a swatch that includes a piece of material and a stain. The stain is then fixed to the material and a smaller swatch can be removed from the swatch. Alternatively, the smaller swatch can be removed from the larger swatch and then the stain can be fixed. Next, an enzyme is applied to the swatch or smaller swatch and they are incubated together.

The method can further include measuring the degree of removal of the stain from the material. The method can also include agitating the smaller swatch and enzyme during incubation. The material can be, for example, cotton, polyester or mixtures of natural and synthetic fibers. The stain can include blood, milk, ink, grass, gravy, chocolate, egg, cheese, clay, pigment, oil, and combinations thereof. The enzyme can be applied to the swatch or smaller swatch in combination with a detergent ingredient.

The present invention also provides a method of assaying for a preferred detergent composition including providing a swatch that includes a piece of material and a stain. The stain is then fixed to the material and a smaller swatch can be removed from the swatch. Alternatively, the smaller swatch can be removed from the larger swatch and then the stain can be fixed. Next, a detergent composition is applied to the swatch or smaller swatch and they are incubated together.

The method can further include measuring the degree of removal of the stain from the material. The method can also include agitating the swatch or smaller swatch and detergent composition during incubation. The material can be, for example, cotton, polyester or mixtures of natural and synthetic fibers, cellulose and derivatives of cellulose. The stain can include blood, milk, ink, grass, spinach, wine, tea, gravy, chocolate egg, cheese, clay, pigment, oil, and combinations thereof. The detergent composition can be applied to the swatch or smaller swatch in combination with an enzyme.

BRIEF DESCRIPTION OF THE DRAWING

FIG. 1 shows the correlation between the results of testing six protease variants in a tergotometer test according to the method of the present invention.

DETAILED DESCRIPTION OF THE INVENTION

One aspect of the present invention is directed to a method of assaying for a preferred enzyme that includes providing a swatch of material—a piece of material and a stain—then fixing the stain to the material, optionally removing a smaller swatch from the swatch, applying the enzyme to the swatch or smaller swatch and incubating them.

A further aspect of the invention is directed to a method of assaying for a preferred detergent composition that includes providing a swatch of material that includes a piece of material and a stain, then fixing the stain to the material, optionally removing a smaller swatch from the swatch, applying the detergent composition to the swatch or smaller swatch and incubating them.

Another aspect of the invention is directed to a method of assaying the release of a stain from a blood/milk/ink (BMI)-stained swatch including measuring the absorbance or fluorescence of, for example, the ink, labeled blood or labeled milk in the supernatant after the swatch has been incubated with an enzyme or detergent composition.

In addition, an aspect of the invention includes a method of agitating the microtiter plate to a sufficient degree to assure complete and efficient incubation of the enzyme with the smaller swatch. The method includes applying a plate sealer to the top of the microtiter plate and then clamping another lid on top of the plate sealer.

Any enzyme or combination of enzymes may be used in the present invention. Preferred enzymes include those enzymes capable of hydrolyzing substrates, e.g. stains. These enzymes are known as hydrolases which include, but are not limited to, proteases (bacterial, fungal, acid, neutral or alkaline), amylases (alpha or beta), lipases, cellulases and mixtures thereof. Particularly preferred enzymes are subtilisins and cellulases. Most preferred are subtilisins such as described in U.S. Pat. No. 4,760,025, EP Patent 130 756 B1 and EP Patent Application WO 91/06637, which are incorporated herein by reference, and cellulases such as Multifect L250™ and Puradax™, commercially available from Genencor International. Other enzymes that can be used in the present invention include oxidases such as laccases, transferases, dehydratases, reductases, hemicellulases and isomerases.

A "swatch" is a piece of material such as a fabric that has a stain applied thereto. The material can be, for example, fabrics made of cotton, polyester or mixtures of natural and synthetic fibers. The swatch can further be paper such as filter paper or nitrocellulose or a piece of a hard material such as ceramic or glass. The stain can be blood, milk, ink, grass, tea, wine, spinach, gravy, chocolate egg, cheese, clay, pigment, oil, or mixtures of these compounds.

A "smaller swatch" is a piece of the swatch that has been cut or otherwise removed from the swatch of material either before or after fixing the stain to the swatch and can, for example, fit into the well of a 24, 48 or 96 well microtiter plate. The "smaller swatch" can also be made by applying a stain to a small piece of material. Preferably, the smaller swatch is a piece of fabric with a stain ⅝" in diameter, more preferably, the smaller swatch is 0.25" in diameter.

When, for example, untreated BMI swatches are washed in detergent without bleach, a large portion of the ink is released even without the help of a protease. Adding a protease leads to a small increase in ink release which can be hard to quantify over the large background. The present invention provides a treatment protocol which allows one to control the degree of fixation of a stain. As a result, it is possible to produce swatches which, for example, release varying amounts of ink when washed in the absence of protease. The use of fixed swatches leads to a dramatic improvement of the signal-to-noise ratio in the wash assays. Furthermore, by varying the degree of fixation one can generate stains which give optimum results under the various cleaning conditions.

Swatches having stains of known "strength" on various types of material are commercially available (EMPA, St. Gallen, Switzerland; wfk—Testgewebe GmbH, Krefeld Germany; or Center for Test Materials, Vlaardingen, The Netherlands) and/or can be made by the practitioner (Morris and Prato, *Textile Research Journal* 52(4):280–286 (1982)). Preferred swatches are a blood/milk/ink (BMI) stain on a cotton-containing fabric, a spinach stain on a cotton-containing fabric, or grass on a cotton-containing fabric, and chocolate/milk/soot on a cotton-containing fabric.

A stain can be fixed to a material in a number of ways. For example, the swatch can be incubated with a cross-linking agent to fix the stain. The degree of fixing can be affected by, for example, increasing or decreasing the incubation time, varying the temperature at which the incubation takes place, and/or varying the concentration of the chemical. Suitable cross-linking agents for use in the present invention include hydrogen peroxide, bleaching agents, glutaraldehyde, and carbodiimides.

In a preferred embodiment of the invention, a BMI stain can be fixed to cotton with 0.0003–0.3% hydrogen peroxide. Other combinations include grass or spinach fixed with 0.001–1% glutaraldehyde, gelatin and Coomassie stain fixed with 0.001–1% glutaraldehyde, or chocolate, milk and soot fixed with 0.001–1% glutaraldehyde.

An important aspect of the present invention is that the swatch and enzyme and/or detergent formulation must be well agitated during incubation. We have observed that the wash performance data is dependent on the orientation of the swatches in the wells (horizontal versus vertical), particularly in the 96-well plate. This would indicate that mixing was insufficient during the incubation period. Although there are a number of ways to ensure sufficient agitation during incubation, a plate holder in which the microtiter plate is sandwiched between two plates of aluminum can be constructed. This can be as simple as placing, for example, an adhesive plate sealer over the wells then clamping the two aluminum plates to the 96-well plate with any type of appropriate, commercially available clamps. It can then be mounted in a commercial incubator shaker. Setting the shaker to about 400 rpm results in very efficient mixing while leakage or cross-contamination is efficiently prevented by the holder.

Trinitrobenzenesulfonic acid (TNBS) can be used to quantify the concentration of amino groups in the wash liquor. This can serve as a measure of the amount of protein that was removed from the swatch (see Cayot and Tainturier, *Anal. Biochem.* 249:184–0200 (1997)). However, if a detergent or an enzyme sample leads to the formation of unusually small peptide fragments (for example, from the presence of peptidases in the sample) then one will obtain a larger TNBS signal, i.e., more "noise".

The present invention provides another and better way to measure wash performance of blood/milk/ink that is based on ink release. Proteolysis of protein on the swatches leads to the release of ink particles which can be quantified by measuring the absorbance of the wash liquor. The absorbance can be measured at any wavelength between 350 and 800 nm. In a preferred embodiment, the wavelength is measured at 410 nm. or 620 nm. The wash liquor can also be examined to determine the wash performance on stains containing grass, spinach, gelatin or Coomassie stain. Preferred wavelengths for these stains include and 670 nm for spinach or grass and 620 nm for gelatin or Coomassie. For example, an aliquot of the wash liquor (typically 100–150 ul from a 96-well microplate, for example) is removed and placed in a cuvette or multiwell microplate. This is then placed in a spectrophotometer and the absorbance is read at an appropriate wavelength The performance of samples of variant proteases (produced, for example, according to the disclosure of U.S. patent application Ser. No. 322,678) by the method of the present invention using TNBS and ink release detection can be compared. Several of these samples show inflated wash performance when TNBS detection is used (probably due to peptidase contamination) whereas all samples result in indistinguishable signals when the absorbance of the wash liquor was measured.

The present invention can also be used to determine a preferred enzyme and/or detergent composition for dish washing, for example, using a blood/milk/ink stain on a suitable substrate such as cloth, plastic or ceramic.

In a preferred embodiment of the invention, a BMI stain is fixed to cotton by applying 0.3% hydrogen peroxide to the BMI/cotton swatch for 30 minutes at 25° C. or by applying 0.03% hydrogen peroxide to the BMI/cotton swatch for 30 minutes at 60° C. Smaller swatches of approximately 0.25" are cut from the BMI/cotton swatch and placed in the wells of a 96 well microtiter plate. Into each well, a known mixture of a detergent composition and an enzyme such as a variant protein is placed. After placing an adhesive plate sealer onto the top of the microtiter plate, the microtiter plate is clamped to an aluminum plate and agitated for 10–300 minutes. At the end of this time, the supernatants are transferred to wells in a new microtiter plate and the absorbance of the ink at 620 nm is measured.

In a further preferred embodiment of the invention, a spinach or grass stain is fixed to cotton by applying 0.01% glutaraldehyde to the spinach/cotton swatch or grass/cotton swatch for 30 minutes at 25° C. Smaller swatches of approximately 0.25" are cut from the swatch and placed in the wells of a 96 well microtiter plate. Into each well, a known mixture of a detergent composition and an enzyme such as a variant protein is placed. After placing an adhesive plate sealer onto the top of the microtiter plate, the microtiter plate is clamped to an aluminum plate and agitated for 10–300 minutes. At the end of this time, the supernatants are transferred to wells in a new microtiter plate and the absorbance of the ink at 670 nm is measured.

In another preferred embodiment of the invention, a chocolate/milk/soot stain is fixed to cotton by applying 0.01% glutaraldehyde to the chocolate/milk/soot/cotton swatch 30 minutes at 25° C. Smaller swatches of approximately 0.25" are cut from the swatch and placed in the wells of a 96 well microtiter plate. Into each well, a known mixture of a detergent composition and an enzyme such as a variant protein is placed. After placing an adhesive plate sealer onto the top of the microtiter plate, the microtiter plate is clamped to an aluminum plate and agitated for 10–300 minutes. At the end of this time, the supernatants are transferred to wells in a new microtiter plate and the absorbance of the ink at an appropriate wavelength is measured.

EXAMPLES

Example I

A. Description of Tergotometer Protocol

A Tergotometer instrument manufactured by United States Testing Company was used. The machine consists of four or six 1.5 liter beakers and agitator spindles which are inserted into the beakers and rotated in a back and forth manner at a controlled speed, typically 100 RPM, to mimic the type of agitation that occurs in commercial washing machines. The beakers are immersed in a temperature controlled water bath.

Each beaker was filled with one liter of deionized water to which a controlled amount of calcium and magnesium were added to mimic water hardness conditions found in the geography under study. Water hardness for North American conditions was set to 3–6 grains per gallon. The water bath was set to 20° C. and the temperature of the water in the beakers was allowed to reach equilibrium at the testing temperature.

1 gram of Tide laundry detergent lacking bleach and enzyme (Procter & Gamble, Cincinnati, Ohio) was added to each beaker and allowed to mix for 1 minute while the spindles were rotating at 100 RPM. The enzyme was added to a final concentration of 0.1 micrograms per milliliter and allowed to mix for 1 minute. Blood-Milk-Ink soiled swatches 3"×4½" obtained from EMPA and modified by exposure to 3.0% hydrogen peroxide for 30 minutes at 20° C. and dried, were used. Six soiled swatches were added to each beaker and allowed to incubate for 20 minutes. After the incubation period the swatches were promptly removed from the beakers and rinsed thoroughly with water. The swatches were then placed flat on a clean lab bench to dry. When the swatches were dry, the reflectance of each swatch was measured at 3 different spots on each swatch, using a reflectance spectrophotometer with a small (typically ¼") diameter aperture, capable of reporting results in the standard LAB scale. For BMI, it is sufficient to report only the L value, which correlates with the darkness of the stain. The L values obtained from the swatches in each pot were averaged to obtain the final reported result.

B. Description of 24-Well Assay Protocol:

Blood-Milk-Ink swatches were obtained from EMPA and were exposed to 0.03% hydrogen peroxide for 30 minutes at 60° C., then dried. Circles of ¼" diameter were cut from the dried swatches and placed one per well in a 24 well microplate. 1 gram per liter Tide laundry detergent without bleach and enzyme was prepared in deionized water, and a concentrated stock of calcium and magnesium was added to result in a final water hardness value of 6 grains per gallon. The detergent was allowed to mix for 15 minutes and was then filtered through a 0.2 micron cellulose acetate filter. Enzyme was added to the filtered detergent from a concentrated stock solution to result in a final concentration of 1.25 micrograms per milliliter. The enzyme/detergent solution was then added to the appropriate wells of the microplate. The microplate was then sealed to prevent leakage and placed in a holder on an incubated shaker set to 20° C. and 400 RPM and allowed to shake for one hour. The plate was then removed from the incubator/shaker and an aliquot of 200 microliters was removed from each well, and the absorbance at 620 nm wavelength was read for each aliquot and reported.

C. Six protease variants were tested according to A and B above. The results are shown in Table 1. The correlation of the data is plotted in FIG. 1. The $R^2$ value is 0.9652.

TABLE 1

| | Tergotometer Microswatch | |
|---|---|---|
| | L Value | Absorbance 620 nm |
| A | 45.62 | 0.066 |
| B | 48.815 | 0.078 |
| C | 51.755 | 0.086 |
| D | 49.06 | 0.076 |
| E | 52.915 | 0.091 |
| F | 53.065 | 0.096 |

The invention claimed is:

1. A method of assaying the wash performance of multiple enzymes comprising:
   a) providing a swatch of material;
   b) fixing a stain to the swatch of material;
   c) cutting the swatch into pieces;
   d) placing the pieces one per well into wells of a 24, 48 or 96 well microtiter plate;
   e) applying the multiple enzymes one per well to the pieces;
   f) incubating the pieces and multiple enzymes while agitating the microtiter plate;
   g) measuring the degree of removal of the stain from the pieces; and
   h) determining the wash performance of the multiple enzymes.

2. The method of claim 1, wherein the multiple enzymes are selected from the group consisting of a protease, a cellulase, an amylase, a laccase, and a lipase.

3. The method of claim 1, wherein the material is selected from the group consisting of a fabric, plastic, glass or ceramic.

4. The method of claim 1, wherein the stain is selected from the group consisting of blood, milk, ink, grass, spinach, gravy, chocolate, egg, cheese, clay, pigment, oil, and combinations thereof.

5. The method of claim 1, wherein the enzymes are applied to the pieces in combination with a detergent ingredient.

6. The method of claim 1 wherein step c) comprises cutting the swatch into approximately 0.25 inch pieces.

7. A method of assaying the wash performance of a detergent composition comprising:
   a) providing a swatches of material;
   b) fixing a stain to each of the swatches of the material;
   c) placing the swatches one per well in wells of a microtiter plate;
   d) applying a detergent and different enzyme to each swatch;
   e) incubating the swatches and detergent and enzymes while agitating the microtiter plate; and
   f) measuring removal of the stain from each swatch to determine wash performance.

8. The method of claim 7, wherein the material is selected from the group consisting of a fabric, plastic, glass, or ceramic.

9. The method of claim 7, wherein the stain is selected from the group consisting of blood, milk, ink, grass, spinach, gravy, chocolate, egg, cheese, clay, pigment, oil, and combinations thereof.

10. The method of claim 7, wherein the detergent is applied to the swatches in combination with the enzymes.

11. The method of claim 10, wherein the enzymes are selected from the group consisting of a protease, a cellulase, an amylase, a laccase, and a lipase.

* * * * *